(12) United States Patent
Müller et al.

(10) Patent No.: US 6,239,192 B1
(45) Date of Patent: May 29, 2001

(54) ACTIVE-SUBSTANCE-CONTAINING MOULDED BODIES BASED ON BIODEGRADABLE THERMOPLASTICALLY PROCESSABLE POLYMERS

(75) Inventors: Hanns Peter Müller, Odenthal; Doris Hackemüller-Bruns, Düsseldorf; Horst Gruttmann, Leverkusen; Kerstin Heeschen, Königswinter, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/297,705

(22) PCT Filed: Oct. 27, 1997

(86) PCT No.: PCT/EP97/05933

§ 371 Date: May 5, 1999

§ 102(e) Date: May 5, 1999

(87) PCT Pub. No.: WO98/19532

PCT Pub. Date: May 14, 1998

(30) Foreign Application Priority Data

Nov. 7, 1996 (DE) .............................................. 196 45 919

(51) Int. Cl.$^7$ ........................................................ C08K 5/56
(52) U.S. Cl. ................................................................ 523/124
(58) Field of Search ............................................... 523/124

(56) References Cited

U.S. PATENT DOCUMENTS 4,554,155 * 11/1985 Allan et al. ............................. 424/22

FOREIGN PATENT DOCUMENTS

WO 91/03940 * 4/1991 (WO).

* cited by examiner

Primary Examiner—Kriellion Sanders
(74) Attorney, Agent, or Firm—Joseph C. Gil; Godfried R. Akorli

(57) ABSTRACT

The present invention relates to new shaped articles which comprise active compounds and are based on thermoplastically processable, biologically degradable polymers, preferably polyesters, polyester amides, polyester urethanes and polyester urethane ureas, and their production and use for combating parasites on, around and in the environment of host animals, the shaped articles optionally serving, after use, for combating phytopathogenic insects on open-air or indoor plants.

7 Claims, No Drawings

ACTIVE-SUBSTANCE-CONTAINING MOULDED BODIES BASED ON BIODEGRADABLE THERMOPLASTICALLY PROCESSABLE POLYMERS

The present invention relates to new shaped articles which comprise active compounds and are based on thermoplastically processable, biologically degradable polymers, preferably polyesters, polyester amides, polyester urethanes and polyesterurethane ureas, and their production and use for combating parasites on, around and in the environment of host animals, the shaped articles optionally serving, after use, for combating phytopathogenic insects on open-air or indoor plants.

Shaped articles which comprise active compounds for controlling pests are known. They are based on the slow release of active compounds from a carrier matrix of plastic which contains active compounds (cf., for example, Aries et al. U.S. Pat. No. 3,814,061, Greeberg U.S. Pat. No. 3,918,407, Miller et al. U.S. Pat. No. 3,944,662, Millionis et al. U.S. Pat. No. 4,041,151, Pasarela U.S. Pat. No. 4,145,409, Greenberg and Cloud U.S. Pat. No. 4,158,051, v. Bittera et al. U.S. Pat. No. 4,225,578, Mc Daniel et al. European Published Specification 0 052 411, Grubb et al. U.S. Pat. No. 3,852,416 and Pearce U.S. Pat. No. 4,536,388).

The carrier employed almost exclusively in known shaped articles in practice is PVC. Although other carriers are mentioned in the literature, to date they have not found acceptance in practice. U.S. Pat. No. 4,195,075 thus mentions, inter alia, that thermoplastic elastomers are also possible carrier polymers for ear tags. However, it is also exclusively examples with plasticized PVC as the carrier polymer which are described in this reference.

This is also not astonishing. PVC is inexpensive and readily accessible. It is also miscible with other substances, in particular plasticizers, in wide ranges. In PVC bodies comprising active compounds, these plasticizers have the function of keeping the active compound dissolved in the carrier and of transporting it slowly to the surface of the body. The active compound evaporates there, or it is rubbed off from the surface together with the plasticizer. The interaction of the three components of PVC carrier, plasticizer and active compound determines whether and to what extent the shaped article can be employed in practice.

If one component of the overall system is changed, it can no longer be predicted whether the system still acts in practice. This applies in particular if the plasticizer, which indeed has a key function in transportation of the active compound, is changed or omitted.

For various reasons, it is desirable to replace PVC as the carrier material.

Shaped articles which contain active compounds and are based on thermoplastically processable elastomers (TPE) are described in EP-A 542 080, 542 081 and 542 078.

The known systems have the disadvantage that their action rapidly becomes inadequate, although often more than 90% by weight of the active compound originally employed is still present in the polymer. This is very uneconomical.

The systems according to the invention allow, after they have been employed for combating parasites on, around and in the environment of host animals, the active compound remaining in them to be utilized economically. For this purpose, they are employed as agents for combating pests on plants in soil, optionally after granulation or grinding.

It was surprising that the shaped articles according to the invention, comprising active compounds, are biologically degraded completely, the active compound contained in them being released. The expert had to expect that the active compounds incorporated into the polymer matrix impede or suppress the biological degradation of polymers which are biologically degradable per se.

The present invention relates to:
1. Shaped articles comprising active compounds, characterized in that they comprise biologically degradable polymers as the carrier, if appropriate plasticizers and if appropriate customary additives.
2. Shaped articles comprising active compounds, characterized in that they comprise biologically degradable polyester amides as the carrier, if appropriate plasticizers and if appropriate customary additives.
3. Process for the production of shaped articles comprising active compounds, characterized in that biologically degradable polymers, preferably thermoplastic polyester amides, are mixed with active compounds, if appropriate plasticizers and if appropriate customary additives and the mixture is processed in the customary manner.
4. Use of the polymer mixtures according to 1 and 2 (above) as shaped articles, preferably tapes, medallions and ear tags, for combating parasites on or around animals, and after use, optionally after comminution, granulation or grinding, as soil granules for combating phytopathogenic insects on open-air or indoor plants.

Biologically degradable polymers are those which meet the test conditions described in the draft specification DIN 54 900-1.

Examples of biologically degradable polymers are polycaprolactone, polycaprolactone-starch blends, aromatic-aliphatic copolyesters, polylactide, polyhydroxybutyrates/valerates and/or starch blends thereof, polyester amides, polyurethanes, polyureas, polyurethane ureas and their blends.

The preparation of suitable polyester amides is described in EP-A 641 817. Reference is made in particular to the polyester amides described therein. Polyester amides are particularly suitable according to the invention.

The preparation and use of thermoplastic polyester urethanes as compostable plastics is described in EP 0 593 975.

The preparation of suitable polyurethane ureas is described in WO 96/35733 and WO 96/38502. Reference is made in particular to the polyurethane ureas described therein. Polyurethane ureas are particularly suitable according to the invention.

Such biologically degradable polyurethanes which can be shaped thermoplastically and contain urea groups are prepared by known processes, adhering to an equivalent ratio of isocyanate groups to groups which are reactive towards isocyanate groups of 1:1 to 2:1, from
a) a diisocyanate component comprising
   a1) hexamethylene diisocyanate or
   a2) mixtures of hexamethylene diisocyanate with a total of up to 60% by weight, based on a mixture, of 1-isocyanato-3,3,5-trimethyl-5-isocyanatomethylcyclohexane and/or 4,4'-diisocyanatodicyclo-hexylmethane and/or 1-methyl-2,4(6)-diisocyanatocyclohexane with
b) a diol component comprising
   b1) at least one polyester diol of molecular weight, which can be calculated from the hydroxyl group content, of 500 to 10,000 from (i) adipic acid and/or succinic acid and (ii) at least one alkanediol having 2 to 6 carbon atoms, or
   b2) a mixture of such polyester diols with up to 32% by weight, based on the total weight of component b), of alkanediols which have 2 to 6 carbon atoms and optionally contain ether groups, c) a diamine component in an amount of 2 to 50 equivalent %, based on the total amount of groups which are reactive towards isocyanate groups and are present in components b) and c), comprising c1) diaminosulphonates of the general formula

or c2) mixtures of diaminosulphonates C1) with up to 90% by weight, based on the total weight of component c), of ethylenediamine, if appropriate d) hydrophilic polyether alcohols of the general formula

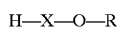

in an amount of up to 10% by weight, based on the total weight of components b), c) and d), and if appropriate e) water, which is not included in the calculation of the equivalent ratio of isocyanate groups to groups which are reactive towards isocyanate groups, wherein, in the general formulae mentioned, m and n independently of one another represent numbers from 2 to 6, Me represents potassium or sodium, R represents a monovalent hydrocarbon radical having 1 to 12 carbon atoms and X denotes a polyalkylene oxide chain of the molecular weight range 88 to 4000, the alkylene oxide units of which comprise ethylene oxide units to the extent of at least 40% and propylene oxide units as the remainder.

The polyurethanes containing urea groups are employed, for example, in the form of 20 to 50, preferably 40 to 50, % strength by weight aqueous dispersions.

Diisocyanate component a) preferably comprises exclusively hexamethylene diisocyanate.

Diol component b) comprises either b1) at least one polyester diol or b2) a mixture of at least one polyester diol b1) with up to 32, preferably up to 10, % by weight of at least one alkenediol which has 2 to 6 carbon atoms and optionally contains ether groups.

Suitable polyester diols b1) are those of a molecular weight, which can be calculated from the hydroxyl group content, of 500 to 10,000, preferably 1000 to 2500, based on (i) adipic acid and/or succinic acid and (ii) alkanediols which have 2 to 6 carbon atoms and optionally contain ether groups, such as, for example, ethylene glycol, diethylene glycol, 1,4-butanediol, neopentyl glycol and/or 1,6-hexanediol. Polyester diols which have been prepared employing exclusively ethylene glycol and/or 1,4-butanediol as the diol are particularly preferred.

The alkanediols which have 2 to 6 carbon atoms, optionally contain ether groups and are optionally to be co-used as chain-lengthening agents containing hydroxyl groups are those of the type just mentioned by way of example.

Diamine component c) comprises either c1) diaminosulphonates of the general formula already mentioned above or c2) mixtures of such diaminosulphonates with ethylenediamine, which is employed, if at all, in amounts of up to 90, preferably up to 70, equivalent %, based on the amino groups of component c) which are reactive towards isocyanate groups. Especially preferred diaminosulphonates are the potassium or sodium salts of N-(2-aminoethyl)-2-aminoethanesulphonic acid.

Diamine component c) is in general co-used in an amount of 1 to 10, preferably 2 to 5, % by weight, based on the weight of component b).

Builder component d) which is optionally to be co-used comprises hydrophilic, monofunctional polyether alcohols of the general formula

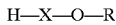

in which

R and X have the meaning already given above.

Preferred such polyether alcohols are those for which

R represents an aliphatic hydrocarbon radical having 1 to 4 carbon atoms and

X represents a polyalkylene oxide chain of the molecular weight range 500 to 4000, in which at least 40, in particular at least 70, and particularly preferably 100% of the alkylene oxide units present are ethylene oxide units and the remaining alkylene oxide units are propylene oxide units.

Such monofunctional polyether alcohols are prepared by alkoxylation, which is known per se, of suitable starter molecules R-OH, such as, for example, methanol, n-butanol, n-hexanol or n-dodecanol, preferably using ethylene oxide and, if appropriate, propylene oxide in the ratios of amounts of the alkylene oxides corresponding to the statements made above. The alkylene oxides mentioned can be employed here as a mixture and/or successively.

The monofunctional polyether alcohols d) are employed, if at all, in amounts of up to 10, preferably up to 3, % by weight, based on the total weight of components b), c) and d).

A further builder component which is optionally possible and may be mentioned for the preparation of the polyurethanes containing urea groups is e) water, which is to be considered a reactant in particular if the chain-lengthening reaction of previously prepared NCO prepolymers which is to be carried out in the last stage of the preparation of the polyurethanes is carried out in an aqueous medium, especially if the diamines c), dissolved in the water, are employed in amounts below the equivalent amounts, based on the NCO groups of the NCO prepolymers.

In addition to these builder components, in principle minor amounts of trifunctional compounds are also possible, such as, for example, glycerol or trimethylolpropane, which can either be incorporated into polyester b1) in small amounts or can be employed in the free form as part of component b2). The co-use of such branching molecules must as a rule be compensated by monofunctional compounds, so that, purely mathematically, linear polymers again result.

The polyurethanes containing urea groups can be prepared from the builder components mentioned by way of example by any desired processes of the prior art. Preferably, however, they are prepared by the known prepolymer process, and in particular such that an NCO prepolymer or semi-prepolymer is prepared from components b) and, if appropriate, d) and diisocyanate component a), adhering to an NCO/OH equivalent ratio of 1.5:1 to 4:1, preferably 1.8:1 to 2.5:1, and this is then reacted with component c), with lengthening of the chain.

In this process, the prepolymer or semi-prepolymer is in general prepared without a solvent at temperatures of 20 to 150° C. and is then dissolved in a suitable solvent. The prepolymer or semi-prepolymer can of course also be formed directly in a solvent. Particularly suitable solvents are solvents which are inert towards isocyanate groups and are of unlimited miscibility with water. Acetone is preferably used as the solvent.

In the second reaction stage, the prepolymers or semi-prepolymers prepared in this way are reacted with component c), with lengthening of the chain. In this reaction, the equivalent ratio of isocyanate groups of the prepolymers or semi-prepolymers on the one hand to amino groups of component c) which are reactive towards isocyanate groups, on the other hand, is 1:1 to 20:1, preferably 1.2:1 to 4:1. The chain-lengthening reaction can be carried out in solution, preferably in acetone solution, or also in an aqueous medium such that the solution of the prepolymers or semi-prepolymers in an organic solvent is combined with a solution of component c) in water, with intensive thorough mixing. As already indicated, a chain-lengthening reaction by reaction of the NCO groups of the prepolymers or semi-prepolymers with the water also takes place here, where appropriate. In the preferred 2-stage preparation mentioned for the polyurethanes containing urea groups, the equivalent ratios between isocyanate groups and groups which are reactive towards isocyanate groups in the two reaction stages is chosen in the context of the disclosure made such that the total ratio of isocyanate groups to groups of components b) to d) which are reactive towards isocyanate groups corresponds to the abovementioned ratio of 1:1 to 2:1. The water is in no case included in the calculation of the equivalent ratios mentioned.

The chain-lengthening reaction is in general carried out within the temperature range of 20 to 50° C.

The shaped articles according to the invention comprise one or more thermoplastically processable, biologically degradable polyester amides. These are understood as meaning polymers of this type which contain aliphatic ester groups and aliphatic amide groups and are compostable, that is to say are already degraded completely under mild conditions under the influence of microorganisms.

Those polyester amides with a random arrangement of the ester and amide segments and with an average molecular weight of between 5000 and 100,000, preferably between 10,000 and 50,000, particularly preferably between 10,000 and 35,000, based on the number-average molecular weight, are preferred.

Particularly preferred polyester amides are those which are derived from monomers from the groups consisting of the dialcohols, such as ethylene glycol, 1,4-butanediol, 1,3-propanediol, 1,6-hexanediol, diethylene glycol and the like, the trialcohols, the dicarboxylic acids, such as oxalic acid, succinic acid, adipic acid and the like, or their methyl, ethyl and the like esters, the hydroxycarboxylic acids, such as lactic acid, and the lactones, such as caprolactone and the like, the amino alcohols, such as ethanolamine, propanolamine and the like, the cyclic lactams, such as ε-caprolactam, lauryl lactam and the like, the ω-aminocarboxylic acids, such as aminocaproic acid and the like, and/or mixtures (1:1 salts) of dicarboxylic acids, such as adipic acid, succinic acid and the like, and diamines, such as hexamethylenediamine, diaminobutane and the like, and/or the polyesters which have hydroxyl or acid end groups and have molecular weights of between 200 and 10,000, as the ester-forming component.

Especially preferred polyester amides are those which are derived from cyclic lactams, such as ε-caprolactam, as the amide-forming component, and 1,4-butanediol and adipic acid, as ester-forming components, and have an ester content of between 30 and 80% by weight, preferably between 35 and 65% by weight, particularly preferably between 35 and 55% by weight.

The polyester amides can comprise 0.1 to 5% by weight, preferably 0.1 to 2% by weight of branching agents. Preferred possible branching agents are trifunctional alcohols, such as trimethylolpropane or glycerol, and furthermore tetrafunctional alcohols, such as pentaerythritol, and also trifunctional carboxylic acids, such as citric acid.

The polyester amides contained in the shaped articles according to the invention are known or can be prepared by known methods (cf. EP-A 0 641 817).

Possible admixed components which the polyester amides can comprise are customary thermoplastically processable and biologically degradable polymers. Preferred possible polymers are polyesters, polyether esters, copolyesters, polyanhydrides, polyester urethane ureas, polyester urethanes, thermoplastic polysaccharides or polysaccharide derivatives, and also polyesters, polyether esters and polyester amides which contain aliphatic and aromatic ester groupings.

Particularly preferred admixing components are polyesters, such as polylactide, polyglycolide, polycaprolactone, polyhydroxyalkanolates, polyaspartic acid and polytartrates, and furthermore thermoplastic polysaccharides, such as cellulose esters, cellulose ethers, cellulose ether esters and starch derivatives, such as starch esters, and also thermoplastic starch.

The content of additional polymer components in the polyester amides can be varied within a relatively wide range, and in particular in general between 1 and 80% by weight, preferably between 5 and 50% by weight.

The shaped articles according to the invention comprise one or more agrochemical active compounds.

Active compounds which may be mentioned for the shaped articles according to the invention are preferably insecticides, in particular parasiticides for use on animals. The insecticides include agonists or antagonists of nicotinergic acetylcholine receptors of insects, phosphorus-containing compounds, such as phosphoric or phosphonic acid esters, naturally occurring and synthetic pyrethroids, carbamates, amidines, juvenile hormones and juvenile hormone-like substances.

Agonists or antagonists of the nicotinergic acetylcholine receptors of insects are known, for example, from European Published Specifications No. 580 553, 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Offenlegungsschrift No. 3 639 877 and No. 3 712 707; Japanese Published Specifications No. 03 220 176, 02 207 083, 63 307 857, 63 287 764, 03 246 283, 04 9371, 03 279 359, 03 255 072; U.S. Pat. Nos. 5,034,524, 4,948,798, 4,918,086, 5,039,686, 5,034,404; PCT Applications No. WO 91/17 659 and No. 91/4965; French Application No. 2 611 114; and Brazilian Application No. 88 03 621.

Reference is herewith expressly made to the compounds described in these publications and their preparation.

These compounds can preferably be represented by the general formula (A)

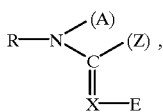
(A)

in which
R represents hydrogen or optionally substituted radicals from the group consisting of acyl, alkyl, aryl, aralkyl, heteroaryl or heteroarylalkyl;
A represents a monofunctional group from the series consisting of hydrogen, acyl, alkyl or aryl, or represents a bifunctional group linked to the radical Z;
E represents an electron-withdrawing group;
X represents the radicals —CH= or =N—, where the radical —CH= can be linked to the radical Z, instead of an H atom;
Z represents a monofunctional group from the series consisting of alkyl, —O—R, —S—R and

or represents a bifunctional group which is linked to the radical A or the radical X.

Particularly preferred compounds of the formula (A) are those in which the radicals have the following meaning:
R represents hydrogen, or optionally substituted radicals from the series consisting of acyl, alkyl, aryl, aralkyl, heteroaryl and heteroarylalkyl.
  Acyl radicals which may be mentioned are formyl, alkylcarbonyl, arylcarbonyl, alkylsulphonyl, arylsulphonyl and (alkyl-)-(aryl)-phosphoryl, which in their turn can be substituted.
  Alkyl which may be mentioned is $C_{1-10}$-alkyl, in particular $C_{1-4}$-alkyl, specifically methyl, ethyl, i-propyl and sec- or t-butyl, which in their turn can be substituted.
  Aryl which may be mentioned is phenyl or naphthyl, in particular phenyl.
  Aralkyl which may be mentioned is phenylmethyl or phenethyl.
  Heteroaryl which may be mentioned is heteroaryl having up to 10 ring atoms and N, O or S, in particular N, as heteroatoms. Thienyl, furyl, thiazolyl, imidazolyl, pyridyl and benzothiazolyl may be mentioned specifically.
  Heteroarylalkyl which may be mentioned is heteroarylmethyl or heteroarylethyl with up to 6 ring atoms and N, O or S, in particular N, as heteroatoms.
  Substitutents which may be mentioned by way of example and as preferred are:
  alkyl having preferably 1 to 4, in particular 1 or 2 carbon atoms, such as methyl, ethyl, n- and i-propyl and n-, i- and t-butyl; alkoxy having preferably 1 to 4, in particular 1 or 2 carbon atoms, such as methoxy, ethoxy, n- and i-propyloxy and n-, i- and t-butyloxy; alkylthio having preferably 1 to 4, in particular 1 or 2 carbon atoms, such as methylthio, ethylthio, n- and i-propylthio and n-, i- and t-butylthio; halogenoalkyl having preferably 1 to 4, in particular 1 or 2 carbon atoms and preferably 1 to 5, in particular 1 to 3 halogen atoms, the halogen atoms being identical or different and being, preferably, fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2 carbon atoms per alkyl group, such as methylamino, methyl-ethylamino, n- and i-propylamino and methyl-n-butylamino; carboxyl; carbalkoxy having preferably 2 to 4, in particular 2 or 3 carbon atoms, such as carbomethoxy and carboethoxy; sulpho (—SO$_3$H); alkylsulphonyl having preferably 1 to 4, in particular 1 or 2 carbon atoms, such as methylsulphonyl and ethylsulphonyl; arylsulphonyl having preferably 6 or 10 aryl carbon atoms, such as phenylsulphonyl, and heteroarylamino and heteroarylalkylamino, such as chloropyridylamino and chloropyridylmethylamino.
A particularly preferably represents hydrogen, and optionally substituted radicals from the series consisting of acyl, alkyl and aryl, which preferably have the meanings given for R. A furthermore represents a bifunctional group. Radicals which may be mentioned are optionally substituted alkylene having 1–4, in particular 1–2 C atoms, substituents which may be mentioned being the substituents listed above and it being possible for the alkylene groups to be interrupted by heteroatoms from the series consisting of N, O and S.
A and Z, together with the atoms to which they are bonded, can form a saturated or unsaturated heterocyclic ring. The heterocyclic ring can contain a further 1 or 2 identical or different heteroatoms and/or hetero groups. Preferred heteroatoms are oxygen, sulphur or nitrogen and preferred hetero groups are N-alkyl, where alkyl of the N-alkyl group preferably contains 1 to 4, in particular 1 or 2 carbon atoms. Alkyl which may be mentioned is methyl, ethyl, n- and i-propyl or n-, i- and t-butyl. The heterocyclic ring contains 5 to 7, preferably 5 or 6 ring members. Examples of the heterocyclic ring which may be mentioned are imidazolidine, pyrrolidine, piperidine, piperazine, hexamethylene imine, hexahydro-1,3,5-triazine, hexahydrooxodiazine and morpholine, which can optionally be substituted, preferably by methyl.
E represents an electron-withdrawing radical, NO$_2$, CN and halogenocarbonyl, such as 1,5-halogeno-$C_{1-4}$-carbonyl, in particular COCF$_3$, being mentioned in particular.
X represents —CH= or —N=
Z represents optionally substituted radicals alkyl, —OR, —SR or —NRR, wherein R and the substituents preferably have the meaning given above.
Z can form, in addition to the abovementioned ring, together with the atom to which it is bonded and the radical

instead of X, a saturated or unsaturated heterocyclic ring. The heterocyclic ring can contain a further 1 or 2 identical or different heteroatoms and/or hetero groups. Heteroatoms are preferably oxygen, sulphur or nitrogen and hetero groups are preferably N-alkyl, where the alkyl of the N-alkyl group preferably contains 1 to 4, in particular 1 or 2 carbon atoms. Alkyl which may be mentioned is methyl, ethyl, n- and i-propyl or n-, i- and t-butyl. The heterocyclic ring contains 5 to 7, preferably 5 or 6 ring members. Examples of the heterocyclic ring which may be mentioned are pyrrolidine, piperidine, piperazine, hexamethylene imine, morpholine and N-methylpiperazine.

Compounds which may be mentioned as compounds which can especially preferably be used according to the invention are those of the general formulae (II) and (III):

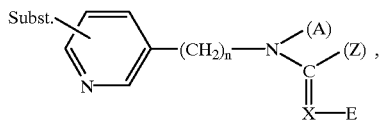
(II)

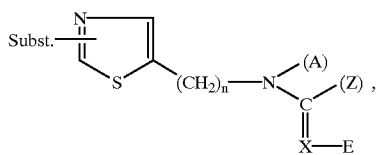
(III)

in which n represents 1 or 2,

Subst. represents one of the abovementioned substituents, in particular halogen, especially chlorine, A, Z, X and E have the meanings given above.

The following compounds may be mentioned specifically:

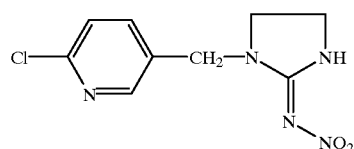

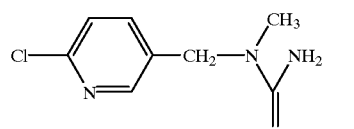

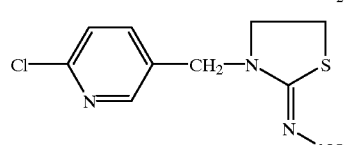

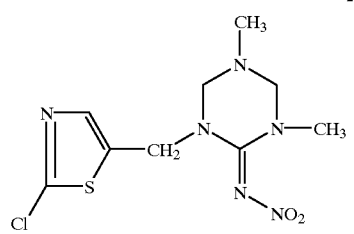

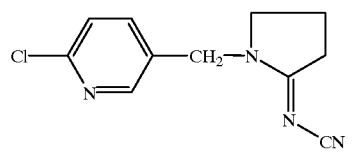

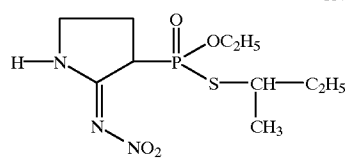

-continued

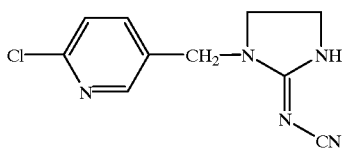

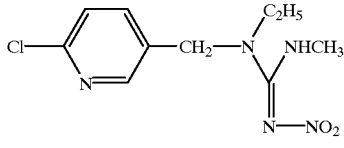

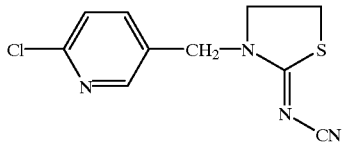

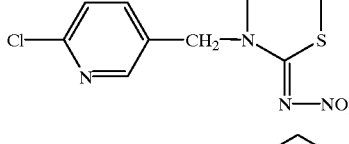

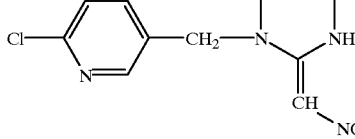

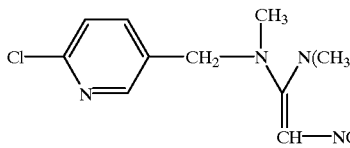

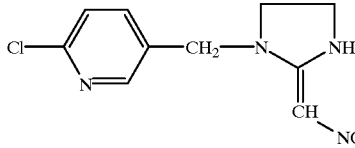

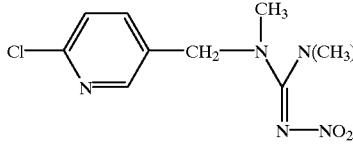

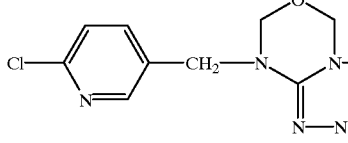

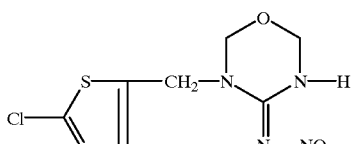

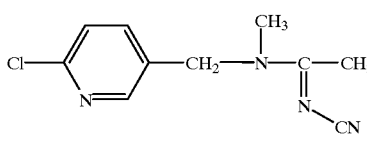

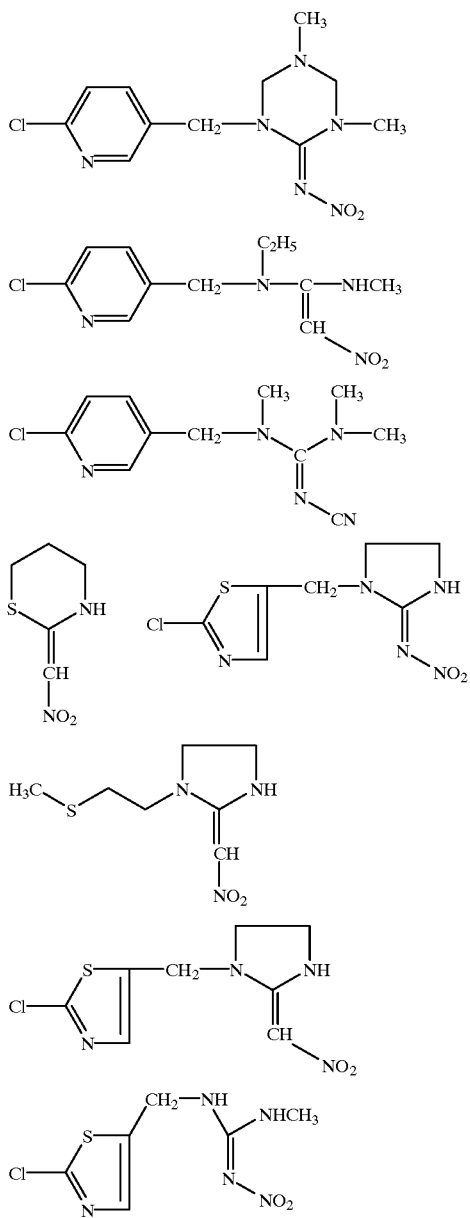

The following compounds may be especially singled out:

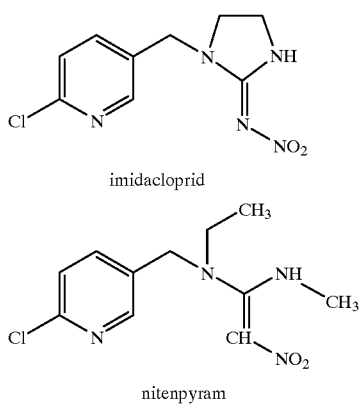

imidacloprid nitenpyram

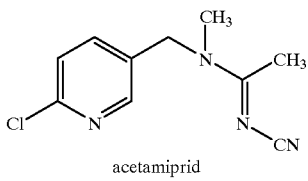

acetamiprid

The phosphoric or phosphonic acid esters include:
O-ethyl O-(8-quinolyl)phenyl thiophosphate (quintiofos),
O,O-diethyl O-(3-chloro-4-methyl-7-coumarinyl) thiophosphate (coumaphos),
O,O-diethyl O-phenylglyoxylonitrile-oxime-thiophosphate (phoxim),
O,O-diethyl O-cyanochlorobenzaldoxime-thiophosphate (chlorphoxim),
O,O-diethyl O-(4-bromo-2,5-dichlorophenyl) phosphorothionate (bromophos-ethyl),
O,O,O',O'-tetraethyl S,S'-methylene-di(phosphorodithionate) (ethion),
2,3-p-dioxanedithiol S,S-bis(O,O-diethylphosphorodithionate,
2-chloro-1-(2,4-dichlorophenyl)-vinyl diethyl phosphate (chlorfenvinphos),
O,O-dimethyl O-(3-methyl-4-methylthiophenyl) thionophosphoric acid ester (fenthion).

The carbamates include:
2-isopropoxyphenyl methylcarbamate (propoxur),
1-naphthyl n-methylcarbamate (carbaryl).

The synthetic pyrethroids include compounds of the formula B

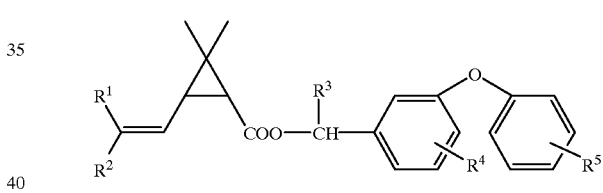

in which
R$^1$ and R$^2$ represent halogen, optionally halogen-substituted alkyl or optionally halogen-substituted phenyl,
R$^3$ represents hydrogen or CN,
R$^4$ represents hydrogen or halogen,
R$^5$ represents hydrogen or halogen.
Preferred synthetic pyrethroids of the formula B are those in which
R$^1$ represents halogen, in particular fluorine, chlorine or bromine,
R$^2$ represents halogen, in particular fluorine, chlorine or bromine, trihalogenomethyl, phenyl or chlorophenyl,
R$^3$ represents hydrogen or CN,
R$^4$ represents hydrogen or fluorine,
R$^5$ represents hydrogen.
Particularly preferred synthetic pyrethroids of the formula B are those in which
R$^1$ represents chlorine,
R$^2$ represents chlorine, trifluoromethyl or p-chlorophenyl,
R$^3$ represents CN,
R$^4$ represents hydrogen or fluorine,
R$^5$ represents hydrogen.
Compounds of the formula B which may be mentioned in particular are those in which
R$^1$ represents chlorine,
R$^2$ represents chlorine or p-chlorophenyl, R³ represents CN,
R⁴ represents fluorine in the 4-position,
R⁵ represents hydrogen.

Compounds which may be mentioned specifically are:
[(α-cyano-4-fluoro-3-phenoxy)benzyl] 3-[2-(4-chlorophenyl)-2-chlorovinyl]-2,2-dimethyl-cyclopropanecarboxylate (flumethrin),
α-cyano-(4-fluoro-3-phenoxy)-benzyl 2,2-dimethyl-3-(2,2-dichlorovinyl)-cyclopropanecarboxylate (cyfluthrin) and its enantiomers and stereoisomers,
α-cyano-3-phenoxybenzyl (±)-cis,trans-3-(2,2-dibromovinyl)-2,2-dimethylcyclo-propanecarboxylate (deltamethrin),
α-cyano-3-phenoxybenzyl 2,2-dimethyl-3-(2,2-dichlorovinyl)-cyclopropanecarboxylate (cypermethrin),
3-phenoxybenzyl (±)-cis,trans-3-(2,2-dichlorovinyl)-2,2-dimethylcyclopropane-carboxylate (permethrin),
α-cyano-3-phenoxy-benzyl α-(p-Cl-phenyl)-isovalerate (fenvalerate),
2-cyano-3-phenoxybenzyl 2-(2-chloro-α,α,α-trifluoro-p-toluidino)-3-methylbutyrate (fluvalinate).

The amidines include:
3-methyl-2-[2,4-dimethyl-phenylimino]-thiazoline
2-(4-chloro-2-methylphenylimino)-3-methylthiazolidine
2-(4-chloro-2-methylphenylimino)-3-(isobutyl-1-enyl)-thiazolidine
1,5-bis-(2,4-dimethylphenyl)-3-methyl-1,3,5-triazapenta-1,4-diene (amitraz).

The juvenile hormones or juvenile hormone-like substances include substituted diaryl ethers, benzoylureas and triazine derivatives. The juvenile hormones and juvenile hormone-like substances include, in particular, compounds of the following formulae:

The substituted diaryl ethers include, in particular, substituted alkoxydiphenyl ethers or -diphenylmethanes of the general formula C wherein
R¹ represents hydrogen, halogen, alkyl, alkoxy, alkylthio, halogenoalkyl, halogenoalkoxy, halogenoalkylthio, dioxyalkylene, dioxyhalogenoalkylene, CN, NO₂, alkenyl, alkinyl, alkoxyalkyl, alkoxyalkoxy or hydroxylalkoxy,
R² represents the radicals given for R¹,
R³ represents the radicals given for R¹,
R⁴ represents hydrogen, alkyl, halogenoalkyl or halogen,
R⁵ represents the radicals given for R⁴,
Het represents optionally substituted heteroaryl which is not bonded to the remainder of the radicals via the heteroatom,
X and Y independently of one another represent —O— or —S—,
Z represents —O—, —S—, —CH₂—, —CHCH₃—, —C(C₃)₂—,
m and n independently of one another represent 0, 1, 2 or 3, but their sum is equal to or greater than 2.

Particularly preferred compounds of the formula C are those
in which
R¹ represents hydrogen, methyl, trifluoromethyl, methoxy, trifluoromethoxy, chlorine or fluorine,
R² represents hydrogen,
R³ represents hydrogen, fluorine, chlorine or methyl,
R⁴ represents hydrogen or methyl,
R⁵ represents methyl, ethyl, trifluoromethyl or hydrogen,
Het represents pyridyl or pyridazinyl, which are optionally substituted by fluorine, chlorine, methyl, NO₂, methoxy or methylmercapto,
X represents O,
Y represents O,
Z represents O, CH₂ or —C(CH₃)₂—,
m represents 1,
n represents 1.

The following compounds may be mentioned specifically:

| R¹ | R³ | R⁵ | R⁶ | Z |
|---|---|---|---|---|
| H | H | CH₃ | H | O |
| H | H | CH₃ | 2-Cl | O |
| 5-F | H | CH₃ | H | O |
| H | H | CF₃ | H | O |
| H | H | C₂H₅ | H | O |
| H | H | H | H | O |
| H | H | CH₃ | H | CH₂ |
| H | H | CH₃ | H | C(CH₃)₂ |

The benzoylureas include compounds of the formula (D):

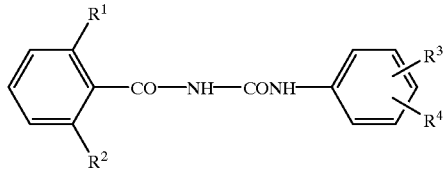

(D)

wherein $R^1$ represents halogen, $R^2$ represents hydrogen or halogen, $R^3$ represents hydrogen, halogen or $C_{1-4}$-alkyl, $R^4$ represents halogen, 1-5-halogeno-$C_{1-4}$-alkyl, $C_{1-4}$-alkoxy, 1-5-halogeno-$C_{1-4}$-alkoxy, $C_{1-4}$-alkylthio, 1-5-halogeno-$C_{1-4}$-alkylthio, phenoxy or pyridyloxy, which can optionally be substituted by halogeno, $C_{1-4}$-alkyl, 1-5-halogeno-$C_{1-4}$-alkyl, $C_{1-4}$-alkoxy, 1-5-halogeno-$C_{1-4}$-alkoxy, $C_{1-4}$-alkylthio, 1-5-halogeno-$C_{1-4}$-alkylthio.

Compounds which may be mentioned in particular are:

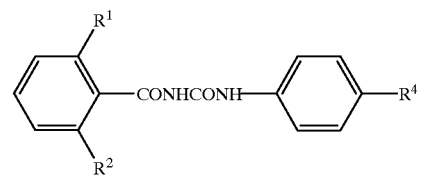

| $R^1$ | $R^2$ | $R^4$ |
|---|---|---|
| H | Cl | $CF_3$ |
| Cl | Cl | $CF_3$ |
| F | F | $CF_3$ |
| H | F | $CF_3$ |
| H | Cl | $SCF_3$ |
| F | F | $SCF_3$ |
| H | F | $SCF_3$ |
| H | Cl | $OCF_3$ |
| F | F | $OCF_3$ |
| H | F | $OCF_3$ |
| F | F | 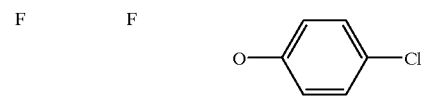 |
| F | F | 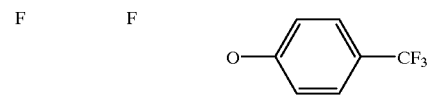 |
| F | F | 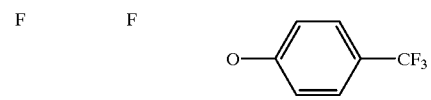 |

The triazines include compounds of the formula (E)

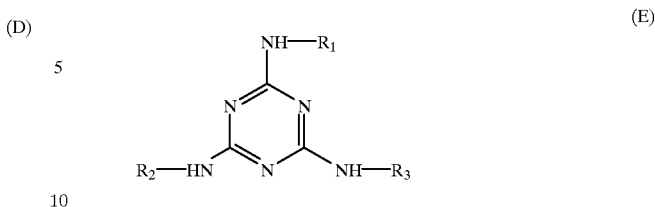

(E)

wherein $R^1$ represents cyclopropyl or isopropyl;

$R_2$ denotes hydrogen, halogen, $C_1$–$C_{12}$-alkylcarbonyl, cyclopropylcarbonyl, $C_1$–$C_{12}$-alkylcarbamoyl, $C_1$–$C_{12}$-alkylthiocarbamoyl or $C_2$–$C_6$-alkenylcarbamoyl; and $R_3$ represents hydrogen, $C_1$–$C_{12}$-alkyl, cyclopropyl, $C_2$–$C_6$-alkenyl, $C_1$–$C_{12}$-alkylcarbonyl, cyclopropylcarbonyl, $C_1$–$C_{12}$-alkylcarbamoyl, $C_1$–$C_{12}$-alkylthiocarbamoyl or $C_2$–$C_6$-alkenylcarbamoyl, and acid addition salts thereof which are non-toxic to warm-blooded animals.

Compounds which may be mentioned in particular are:

| $R^1$ | $R^2$ | $R^3$ |
|---|---|---|
| Cyclopropyl | H | H |
| Cyclopropyl | H | $CH_3$ |
| Cyclopropyl | H | $C_2H_5$ |
| Cyclopropyl | H | $C_3H_7$-n |
| Cyclopropyl | H | $C_4H_9$-n |
| Cyclopropyl | H | $C_5H_{11}$-n |
| Cyclopropyl | H | $C_6H_{13}$-n |
| Cyclopropyl | H | $C_7H_{15}$-n |
| Cyclopropyl | H | $C_8H_{17}$-n |
| Cyclopropyl | H | $C_{12}H_{25}$-n |
| Cyclopropyl | H | $CH_2$—$C_4H_9$-t |
| Cyclopropyl | H | $CH_2CH(CH_3)C_2H_5$ |
| Cyclopropyl | H | $CH_2CH=CH_2$ |
| Cyclopropyl | Cl | $C_2H_5$ |
| Cyclopropyl | Cl | $C_6H_{13}$-n |
| Cyclopropyl | Cl | $C_8H_{17}$-n |
| Cyclopropyl | Cl | $C_{12}H_{25}$-n |
| Cyclopropyl | H | Cyclopropyl |
| Cyclopropyl | H | $COCH_3$ |
| Cyclopropyl | H | $COCH_3$.HCl |
| Cyclopropyl | H | $COC_2H_5$.HCl |
| Cyclopropyl | H | $COC_2H_5$ |
| Cyclopropyl | H | $COC_3H_7$-n |
| Cyclopropyl | H | $COC_3H_7$-i |
| Cyclopropyl | H | $COC_4H_9$-t.HCl |
| Cyclopropyl | H | $COC_4H_9$-n |
| Cyclopropyl | H | $COC_6H_{13}$-n |
| Cyclopropyl | H | $COC_{11}H_{23}$-n |
| Cyclopropyl | $COCH_3$ | $COC_2H_5$ |
| Cyclopropyl | $COC_3H_7$-n | $COC_6H_{13}$-n |
| Cyclopropyl | $COCH_3$ | $COC_3H_7$-n |
| Cyclopropyl | $COC_2H_5$ | $COC_3H_7$-n |
| Cyclopropyl | H | COCyclopropyl |
| Cyclopropyl | COCyclopropyl | COCyclopropyl |
| Cyclopropyl | $COCH_3$ | $COCH_3$ |
| Isopropyl | H | H |
| Isopropyl | H | $COCH_3$ |
| Isopropyl | H | $COC_3H_7$-n |
| Cyclopropyl | H | $CONHCH_3$ |
| Cyclopropyl | H | $CONHC_3H_7$-i |
| Cyclopropyl | $CONHCH_3$ | $CONHCH_3$ |
| Cyclopropyl | H | $CSNHCH_3$ |
| Cyclopropyl | H | $CONHCH_2CH=CH_2$ |
| Cyclopropyl | $CONHCH_2CH=CH_2$ | $CONHCH_2CH=CH_2$ |
| Cyclopropyl | $CSNHCH_3$ | $CSNHCH_3$ |

The active compounds with the common names propoxur, cyfluthrin, flumethrin, pyriproxyfen, methoprene, diazinon, amitraz, fenthion and imidacloprid may be singled out in particular.

The active compounds can be present in the shaped articles by themselves or as a mixture with one another.

The active compounds are present in the shaped articles in concentrations of 0.1–20% by weight, preferably between 1 and 10% by weight.

If appropriate, the shaped articles according to the invention comprise plasticizers. Plasticizers for biologically degradable polymers which are suitable for use on animals comprise the following substance classes: glycerol esters, citric acid esters, lactic acid esters, glycerol, myristic acid esters, adipic acid esters and, where appropriate, phthalic acid esters.

The plasticizers are present in the shaped articles in concentrations of not more than 40% by weight, preferably between 0 and 30% by weight.

The shaped articles according to the invention can furthermore comprise the additives customary for plastics. Customary additives are, for example, pigments, stabilizers, flow agents, lubricants, mould release agents and fillers.

Examples of customary additives are:
1. Antioxidants, which include
1.1 Alkylated monophenols, for example 2,6-di-tert-butyl-4-methylphenol, 2-tert-butyl-4,6-dimethylphenol, 2,6-di-tert-butyl-4-ethyl-4-ethylphenol, 2,6-di-tert-butyl-4-n-butylphenol, 2,6-di-tert-butyl-4-i-butylphenol, 2,6-di-cyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxy-methylphenol.
1.2 Alkylated hydroquinones, for example 2,6-di-tert-butyl-4-methoxyphenol, 2,5-di-tert-butyl-hydroquinone, 2,5-di-tert-amyl-hydroquinone, 2,6-diphenyl-4-octadecyloxyphenyl.
1.3 Hydroxylated thiodiphenyl ethers, for example 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).
1.4 Alkylidene-bisphenols, for example 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)-phenol), 2,2'-methylene-bis-(4-methyl-6-cyclohexyl-phenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4-isobutyl-phenol), 2,2'-methylene-bis-[6-(α-methylbenzyl)-4-nonylphenol], 2,2'-methylene-bis-[6-(α,α-dimethylbenzyl)4-nonylphenol], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxybenzyl)4-methylphenol, 1,1,3-tris-(5-tert-butyl-4-hydroxy-2-methylphenyl)-butane, 1,1-bis-(5-tert-butyl-4-hydroxy-2-methylphenyl)-3-n-dodecylmercaptobutane, ethylene glycol-bis-[3,3-bis-(3'-tert-butyl-4'-hydroxyphenyl)-butyrate], di-(3-tert-butyl-4-hydroxy-5-methylphenyl)-dicyclopentadiene, di-[2-(3'-tert-butyl-2'-hydroxy-5'-methylbenzyl)-6-tert-butyl-4-methyl-phenyl]-terephthalate.
1.5 Benzyl compounds, for example 1,3,5-tri-(3,5-di-tert-butyl-4-hydroxybenzyl)-2,4,6-trimethylbenzene, di-(3,5-di-tert-butyl-4-hydroxybenzyl) sulphide, isooctyl 3,5-di-tert-butyl-4-hydroxybenzyl-mercaptoacetate, bis-(4-tert-butyl-3-hydroxy-2,6-dimethylbenzyl) dithiol-terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzyl-phosphonate, 3,5-di-tert-butyl-4-hydroxybenzyl-phosphonic acid monoethyl ester, calcium salt.
1.6 Acylaminophenols, for example 4-hydroxy-lauric acid anilide, 4-hydroxystearic acid anilide, 2,4-bis-octylmercapto-6-(3,5-di-tert-butyl-4-hydroxyanilino)-s-triazine, octyl N-(3,5-di-tert-butyl-4-hydroxyphenyl)-carbamate.
1.7 Esters of β-(3,5-di-tert-butyl-4-hydroxyphenyl)-propionic acid with mono- or polyhydric alcohols, such as, for example, methanol, octadecanol, 1,6-hexanediol, neopentyl glycol, thiodiethylene glycol, diethylene glycol, triethylene glycol, pentaerythritol, tris-hydroxyethyl isocyanurate, di-hydroxyethyl-oxalic acid diamide.
1.8 Esters of β-(5-tert-butyl-4-hydroxy-3-methylphenyl)-propionic acid with mono- or polyhydric alcohols, such as, for example, methanol, octadecanol, 1,6-hexanediol, neopentyl glycol, thiodiethylene glycol, diethylene glycol, triethylene glycol, pentaerythritol, tris-hydroxyethyl isocyanurate, di-hydroxyethyl-oxalic acid diamide.
1.9 Amides of β-(3,5-di-tert-butyl-4-hydroxyphenyl)-propionic acid, such as, for example,
N,N'-di-(3,5-di-tert-butyl-4-hydroxyphenylpropionyl)-hexamethylene diamine, N,N'-(3,5-di-tert-butyl-4-hydroxyphenylpropionyl)-trimethylene diamine, N,N-di-(3,5-di-tert-butyl-4-hydroxyphenylpropionyl)-hydrazine.
2. UV absorbers and light stabilizers, which include
2.1 2-(2'-hydroxyphenyl)benzotriazoles, such as, for example, the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl, 3',5'-bis-(α,α-dimethylbenzyl) derivative.
2.2 2-hydroxybenzophenones, such as, for example, the 4-hydroxy, 4-methoxy, 4-octoxy, 4-decyloxy, 4-dodecyloxy, 4-benzyloxy, 4,2',4'-trihydroxy, 2'-hydroxy-4,4'-dimethoxy derivative.
2.3 Esters of optionally substituted benzoic acids, such as, for example, 4-tert-butyl-phenyl salicylate, phenyl salicylate, octylphenyl salicylate, dibenzoyl resorcinol, bis-(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate.
2.4 Acrylates, such as, for example, ethyl or isooctyl α-cyano-β,β-diphenylacrylate, methyl α-carbomethoxy-cinnamate, methyl or butyl α-cyano-β-methyl-p-methoxy-cinnamate, methyl α-carbomethoxy-p-methoxy-cinnamate, N-(β-carbomethoxy-β-cyanovinyl)-2-methyl-indoline.
2.5 Nickel compounds, such as, for example, nickel complexes of 2,2'-thio-bis-[4-(1,1,3,3-tetramethylbutyl)-phenol], such as the 1:1 or 1:2 complex, optionally with additional ligands, such as n-butylamine, triethanolamine or N-cyclohexyldiethanolamine, nickel dibutyl-dithiocarbamate, nickel salts of 4-hydroxy-3,5-di-tert-butylbenzyl-phosphonic acid monoalkyl esters, such as of the methyl or ethyl ester, nickel complexes of ketoximes, such as of 2-hydroxy-4-methyl-phenyl undecyl ketone oxime, nickel complexes of 1-phenyl-4-lauroyl-5-hydroxypyrazole, optionally with additional ligands.
2.6 Sterically hindered amines, such as, for example, bis-(2,2,6,6-tetramethylpiperidyl) sebacate, bis-(1,2,2,6,6-pentamethylpiperidyl) sebacate, bis-(1,2,2,6,6- pentamethylpiperidyl) n-butyl-3,5-di-tert-butyl-4-hydroxy-benzyl-malonate, condensation product of 1-hydroxyethyl-2,2,6,6-tetramethyl-4-hydroxypiperidine and succinic acid, condensation product of N,N'-(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl)nitrotriacetate, tetrakis-(2,2,6,6-tetramethyl-4-piperidyl)-1,2,3,4-butane-tetracarboxylic acid, 1,1'-(1,2-ethanediyl)-bis-(3,3,5,5-tetramethyl-piperazinone).

2.7. Oxalic acid diamides, such as, for example, 4,4'-dioctyloxy-oxanilide, 2,2'-dioctyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethyloxy-5-tert-butyl-2'-ethyloxanilide and a mixture thereof with 2-ethoxy-2'-ethyl-5,4'-di-tert-butyl-oxanilide, mixtures of o- and p-methoxy- and of o- and p-ethoxy-disubstituted oxanilides.

3. Metal deactivators, such as, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, such as, for example, triphenyl phosphite, diphenyl alkyl phosphites, phenyl dialkyl phosphites, tri-(nonylphenyl)-phosphite, trilauryl phosphite, trioctadecyl phosphite, distearyl pentaerythritoldiphosphite, tris-(2,4-di-tert-butylphenyl) phosphite, diisodecyl pentaerythritol-diphosphite, di-(2,4-di-tert-butylphenyl) pentaerythritol diphosphite, tristearyl sorbitol-triphosphite, tetrakis-(2,4-di-tert-butylphenyl) 4,4'-biphenylene-diphosphonite, 3,9-bis-(2,4-di-tert-butylphenoxy-2,4,8,10-tetraoxa-3,9-diphosphaspiro[5.5]undecane.

5. Peroxide-destroying compounds, such as, for example, esters of β-thiodipropionic acid, for example the lauryl, stearyl, myristyl or tridecyl ester, mercaptobenzimidazole, the zinc salt of 2-mercaptobenzimidazole, zinc dibutyl-dithiocarbamate, dioctadecyl disulphide and pentaerythritol tetrakis-(β-dodecylmercapto)-propionate.

6. Polyamide stabilizers, such as, for example, copper salts in combination with iodides and/or phosphorus compounds and salts of divalent manganese.

7. Basic co-stabilizers, such as, for example, melamine, polyvinylpyrrolidone, dicyandiamide, triallyl cyanurate, urea derivatives, amines, polyamides, polyurethanes, alkali metal and alkaline earth metal salts of higher fatty acids, for example Ca stearate, Zn stearate, Mg stearate, Na ricinoleate, K palmitate, antimony pyrocatecholate or tin pyrocatecholate.

8. Nucleating agents, such as, for example, 4-tert-butyl benzoic acid, adipic acid, diphenylacetic acid.

9. Fillers and reinforcing agents, such as, for example, calcium carbonate, silicates, glass fibres, talc, kaolin, mica, barium sulphate, metal oxides and hydroxides, carbon black, graphite.

10. Other additives, such as, for example, lubricants, emulsifiers, pigments, optical brighteners, flameproofing agents, antistatics, blowing agents.

In the production of the shaped articles according to the invention, the various constituents can be mixed in the dry state by known mixing processes and pressed into shape by known extrusion or injection-moulding processes.

It is furthermore possible to mix the individual components by dissolving them in a common solvent and then precipitating them in a suitable non-solvent or freeing the solution from the solvent via an evaporating extruder. During the precipitation, the solution is preferably forced through a nozzle into a precipitating bath and the coagulating material formed is drawn off as filaments (wet spinning process). The precipitation is preferably carried out by means of the known dry and wet spinning processes.

The choice of processing process for the production of the shaped articles according to the invention in principle depends technically on the rheological properties of the shaped article material and the shape of the desired structure. The processing processes can be adjusted according to the processing technology or according to the nature of the shaping. The processes can be classified in process technology according to the rheological states which they pass through. Accordingly, casting, pressing, spraying and application are possible for viscous shaped article materials, and injection moulding, extrusion, calendering, milling and, where appropriate, kneading are possible for elastoviscous polymers. Classified according to the nature of the shaping, the shaped articles according to the invention can be produced by casting, dipping, pressing, injection moulding, extrusion, calendering, embossing, bending, thermoforming, spinning and the like.

These processing processes are known and require no more detailed explanation.

Shaped articles according to the present invention are collars, tags for collars (medallions), ear, tail and foot tapes, ear tags, films, peel-off films, adhesive strips, strips, sheets and granules. Collars and medallions for dogs and cats may be mentioned as preferred.

The shaped articles are used for combating parasites on the host animal, at the host animal and in the environment of host animals, such as domestic animals, pets and stock animals.

The domestic animals, pets and stock animals include mammals, such as, for example, cattle, sheep, goats, horses, pigs, dogs, cats.

The pests include:

from the order of the Anoplura, for example, Haematopinus spp., Linognathus spp., Solenopotes spp., Pediculus spp., Pthirus spp.;

from the order of the Mallophaga, for example, Trimenopon spp., Menopon spp., Eomenacanthus spp., Menacanthus spp., Trichodectes spp., Felicola spp., Damalinea spp., Bovicola spp.;

from the order of the Diptera, for example, Aedes spp., Culex spp., Simulium spp., Phlebotomus spp., Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma spp., Oestrus spp., Rhinoestrus spp., Melophagus spp., Hippobosca spp.

From the order of the Siphonaptera, for example, Ctenocephalides spp., Echidnophaga spp., Ceratophyllus spp.

From the order of the Metastigmata, for example, hyalomma spp., Rhipicephalus spp., Boophilus spp., Amblyomma spp., Haemaphysalis spp., Dermacentor spp., Ixodes spp., Argas spp., Ornithodorus spp., Otobius spp.;

and from the order of the Mesotigmata, for example, Dermanyssus spp., Ornithonyssus spp., Pneumonyssus spp.

From the order of the Prostigmata, for example, Cheyletiella spp., Psoregates spp., Myobia spp., Demodex spp., Neotrombicula spp.;

from the order of the Astigmata, for example, Acarus spp., Myocoptes spp., Psoroptes spp., Chorioptes spp., Otodectes spp., Sarcoptes spp., Notoedres spp., Knemidocoptes spp., Neoknemidocoptes spp., Cytodites spp., Laminosioptes spp.

As already mentioned, after use the shaped articles according to the invention can be granulated and ground and the material obtained as a result can be employed for combating phytopathogenic insects in the field of agriculture or cultivation of garden and ornamental plants.

The pests which occur in the fields mentioned include:

from the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Dermaptera, for example, *Forficula auricularia.*

From the order of the Isoptera, for example, Reticulitermes spp.

From the order of the Mallophaga, for example, Trichodectes spp., Damalinea spp.

From the order of the Thysanoptera, for example, *Hercinothrips femoralis, Thrips tabaci.*

From the order of the Heteroptera, for example, Eurygaster spp., *Dysdercus intermedius, Piesma quadrata, Cimex lectularius, Rhodnius prolixus,* Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica.*

From the order of the Hymenoptera, for example, Diprion spp., Hoplocampa spp., Lasius spp., *Monomorium pharaonis,* Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa.*

From the order of the Siphonaptera, for example, *Xenopsylla cheopis,* Ceratophyllus spp.

From the order of the Arachnida, for example, *Scorpio maurus, Latrodectus mactans.*

The following examples describe insecticidal shaped articles and their production on the basis of biologically degradable polymers, which are intended to illustrate the invention without limiting it.

A condensate of adipic acid, 1,4-butanediol and ε-caprolactam was employed as the polyester amide in the examples. The synthesis and biological degradability are described in EP-A 641 817. The polyester amide employed in the examples comprises 60% by weight amide contents and 40% by weight ester contents, which are distributed randomly over the macromolecule.

A solid, the preparation of which is described in Example 1 in WO 96/1780, was employed as the polyurethane urea.

The polyurethane used in Examples 8 to 11 was prepared in accordance with EP 0 593 975 Example 2 and comprises 85.22% by weight of aliphatic polyester units built up from adipic acid, ethylene glycol, neopentyl glycol and hexanediol, 12.4% by weight of hexamethylene diisocyanate (HDI) and 2.33% by weight of butanediol.

In carrying out the process according to the invention, a procedure is in general followed in which the components are mixed with one another in the desired amounts in any desired sequence and the mixture is then heated to temperatures of between 50° C. and 180° C., preferably between 60° C. and 160° C., while stirring or kneading. The pasty composition or liquid mixture formed as a result can be converted into shaped articles or films by the methods customary for thermoplastically processable polymers, with the aid of nozzles, presses or other suitable devices.

EXAMPLES

Example 1

72 g of polyester amide and 11.1 g of triacetin were premixed at 130° C. in a Haake kneader at 25 rpm, 6.9 g of imidacloprid were introduced and the components were kneaded at 50 rpm for about 10 minutes until a homogeneous mass was obtained. The mixture was pressed to a test sheet 1 mm thick at 120° C. under 200 bar in the course of 2 minutes. A strip of 180×50×1 mm was stored in the open and the active compound released was wiped off from the surface with water from time to time and determined quantitatively via HPLC.

| Storage [days] | 29 | 50 | 64 | 78 | 92 | 106 | 120 | 141 |
|---|---|---|---|---|---|---|---|---|
| Active compound released [mg] | 2.82 | 2.55 | 3.14 | 2.14 | 1.77 | 1.12 | 3.87 | 3.29 |

The procedure in Examples 2 to 11 was as in Example 1.

In Examples 12 to 19, the aqueous dispersion, the plasticizer and the active compound were mixed and the mixture was dried and pressed as in Example 1.

Example 2
Composition:
  60% by weight of polyester amide
  30% by weight of ethyl lactate
  10% by weight of imidacloprid

| Storage [days] | 5 | 26 | 40 | 54 |
|---|---|---|---|---|
| Active compound released [mg] | 1.38 | 1.73 | 1.90 | 1.17 |

Example 3
Composition:
  60% by weight of polyester amide
  30% by weight of diacetin
  10% by weight of imidacloprid

| Storage [days] | 5 | 26 | 40 | 54 |
|---|---|---|---|---|
| Active compound released [mg] | 3.04 | 2.87 | 3.44 | 2.50 |

Example 4
Composition:
  95% by weight of polyester amide
  5% by weight of imidacloprid

| Storage [days] | 6 | 20 | 34 |
|---|---|---|---|
| Active compound released [mg] | 3.49 | 3.08 | 1.08 |

Example 5
Composition:
  98% by weight of polyester amide
  2% by weight of imidacloprid

| Storage [days] | 6 | 20 | 34 |
|---|---|---|---|
| Active compound released [mg] | 1.02 | 0.56 | 0.55 |

Example 6
Composition:
  90% by weight of polyester amide
  5% by weight of triacetin
  5% by weight of imidacloprid

| Storage [days] | 6 | 20 | 34 |
|---|---|---|---|
| Active compound released [mg] | 4.13 | 6.11 | 1.96 |

Example 7
Composition:
  96% by weight of polyester amide
  2% by weight of triacetin
  2% by weight of imidacloprid

| Storage [days] | 6 | 20 | 34 |
|---|---|---|---|
| Active compound released [mg] | 1.29 | 5.73 | 0.72 |

Example 8
Composition:
  90% by weight of polyurethane
  5% by weight of imidacloprid

| Storage [days] | 6 | 20 | 34 |
|---|---|---|---|
| Active compound released [mg] | 3.98 | 2.70 | 1.50 |

Example 9
Composition:
  95% by weight of polyurethane
  5% by weight of imidacloprid

| Storage [days] | 6 | 20 | 34 |
|---|---|---|---|
| Active compound released [mg] | 4.93 | 2.85 | 1.54 |

Example 10
Composition:
  80% by weight of polyurethane
  10% by weight of triacetin
  10% by weight of imidacloprid

| Storage [days] | 6 | 20 | 34 |
|---|---|---|---|
| Active compound released [mg] | 3.79 | 2.99 | 1.46 |

Example 11
Composition:
  90% by weight of polyurethane
  5% by weight of triacetin
  5% by weight of imidacloprid

| Storage [days] | 6 | 20 | 34 |
|---|---|---|---|
| Active compound released [mg] | 4.42 | 3.05 | 1.36 |

Example 12
Composition:
  95% by weight of polyurethane urea
  5% by weight of imidacloprid

| Storage [days] | 6 | 20 | 34 |
|---|---|---|---|
| Active compound released [mg] | 4.75 | 3.29 | 1.42 |

Example 13
Composition:
  98% by weight of polyurethane urea
  2% by weight of imidacloprid

| Storage [days] | 6 | 20 | 34 |
|---|---|---|---|
| Active compound released [mg] | 2.38 | 4.24 | 0.91 |

Example 14
Composition:
  90% by weight of polyurethane urea
  5% by weight of triacetin
  5% by weight of imidacloprid

| Storage [days] | 6 | 20 | 34 |
|---|---|---|---|
| Active compound released [mg] | 3.62 | 2.66 | 1.65 |

Example 15
Composition:
  96% by weight of polyurethane urea
  2% by weight of triacetin
  2% by weight of imidacloprid

| Storage [days] | 6 | 20 | 34 |
|---|---|---|---|
| Active compound released [mg] | 2.14 | 2.36 | 1.67 |

Example 16
Composition:
  90% by weight of polyurethane urea
  2% by weight of imidacloprid

| Storage [days] | 9 | 23 | 37 | 51 | 65 | 86 |
|---|---|---|---|---|---|---|
| Active compound released [mg] | 1.80 | 1.75 | 0.98 | 1.50 | 1.89 | 3.67 |

Example 17
Composition:
  80% by weight of polyurethane urea
  10% by weight of glycerol
  10% by weight of imidacloprid

| Storage [days] | 9 | 23 | 37 | 51 | 65 | 86 |
|---|---|---|---|---|---|---|
| Active compound released [mg] | 1.53 | 2.26 | 1.43 | 2.30 | 3.30 | 5.23 |

Example 18
Composition:
  80% by weight of polyurethane urea
  10% by weight of diacetin
  10% by weight of imidacloprid

| Storage [days] | 9 | 23 | 37 | 51 | 65 | 86 |
|---|---|---|---|---|---|---|
| Active compound released [mg] | 1.74 | 1.96 | 2.06 | 1.87 | 2.07 | 2.88 |

Example 19
Composition:
  80% by weight of polyurethane urea
  10% by weight of triacetin
  10% by weight of imidacloprid

| Storage [days] | 9 | 23 | 37 | 51 | 65 | 86 |
|---|---|---|---|---|---|---|
| Active compound released [mg] | 1.66 | 3.20 | 1.28 | 3.20 | 3.23 | 3.70 |

Example 20

A test sheet according to Example 1 was cut into 1.4 cm (commercially available width of collars) strips with an impact cutter. The collars formed therefrom were fitted as tightly as possible (with an intermediate space of a finger-width) on the neck of the animals. Testing was carried out on 4 dogs (beagles). Four further dogs were used as untreated control. The animals were infested twice before and at weekly intervals after the treatment with about 100 fleas [cat flea, *C. felis* (Siphonaptera: Pulicidae) fasting, imagines up to a maximum of 4 weeks old] in the region of the inside of the femur. The following conclusions were drawn from the data determined: within 24 hours after treatment, the dogs were free from fleas. The duration of the activity determined in this test is at least 115 days. Thereafter, the collar was removed and a residual activity of a maximum of 7 weeks was determined with the aid of continued exposure to infestation.

Example A
Preparation of a Dispersion of a Polyurethane Urea 170 g of a polyester diol of molecular weight 1700 from adipic acid and a mixture of 1,6-hexanediol and neopentyl glycol in a weight ratio of 1.9:1 are degassed in vacuo at 120° C. for 60 minutes. 0.2 ml of benzoyl chloride and, all at once, 30.1 g of hexamethylene diisocyanate are added to the batch, under nitrogen. After the mixture has been stirred at 120° C. for 30 minutes, the NCO content is 3.2%. The prepolymer is dissolved in 500 g of acetone at 50° C., the solution is cooled to room temperature and a mixture of 9.7 g of a 50% strength aqueous solution of AAS salt and 1.51 g of ethylenediamine and 20 g of water is added to the acetone solution, while stirring rapidly. After the mixture has been stirred for 15 minutes, 300 g of water are added and the acetone is removed up to 60° C. under 140 mbar. 505 g remain as the distillation residue. After dilution with 11 g of water, a 40% strength, thinly liquid white polyurethane urea dispersion is obtained.

A sample of the dispersion is diluted with water, poured onto a glass plate and dried. A clear, non-tacky film with an elongation at break of not more than 200% is obtained. The layer thickness is 0.25 mm.

Example B

Polyester amide from an oligoester, with acid end groups, from adipic acid and butanediol and from hexamethylene diamene and ε-caprolactam with an ester content of 40% by weight.

346 g (1 mol) of oligoester, with acid end groups, from butanediol and adipic acid (AN 320), 116 g (1 mol) of 1,6-hexamethylene diamine and 72.3 g (0.64 mol) of caprolactam are brought together and the mixture is heated up slowly to 170° C. in an autoclave under the autogenous pressure. After a period of 3 hours, the autoclave is let down and water is distilled off. Depending on the vigorousness of the distillation, the mixture is heated up to 220° C. and a vacuum is applied. Finally, the polymerization is brought to conclusion at 240° C. with an oil pump vacuum for 4 hours. A pale yellow product which can be granulated is obtained. The melting point according to DSC is 123° C. The relative viscosity (1% strength by weight in m-kresol at 25° C.) is 2.8.

In the biological degradation test, the material shows a microbe growth of 102 mg in 14 days.

Example C 267.0 g of an oligoester, with hydroxyl end groups, from adipic acid and hexanediol/neopentyl glycol (molar ratio 3:1) with an average molecular weight of 1790 g/mol and 117.4 g of an oligoester, with hydroxyl end groups, from ethylene glycol and adipic acid with an average molecular weight of 1957 g/mol are heated to 140° C., and degassed in vacuo for 30 minutes. 10.8 g of 1,4-butanediol are then added and degassing is carried out at 140° C. for a further 10 minutes. Thereafter, 0.1 g of dibutyltin dilaurate and 57.2 g of hexamethylene diisocyanate are added and the mixture is stirred rapidly until it becomes viscous. The mass is poured out onto a metal sheet and heat-treated at 100° C. for 10 hours.

A light-coloured flexible material which allows at least 60 mg/l of biomass growth after two weeks under the test conditions described in the text is obtained.

What is claimed is:

1. Shaped articles comprising active compounds, characterized in that they are capable of being used in said shaped form, and in a granulated form for a second use said shaped articles comprise biologically degradable polymers selected from the group consisting of polycaprolactone, polycaprolactone-starch blends, aromatic-aliphatic copolyesters, polylactide, polyhydroxybutyrates/valerates and/or starch blends thereof, polyester amides, polyurethanes, polyureas, polyurethane ureas and their blends as the carrier, and optionally plasticizers and additives.

2. Shaped articles comprising active compounds, characterized in that they comprise biologically degradable polyester amides as the carrier, and optionally plasticizers and optionally customary additives.

3. Process for the production of shaped articles comprising active compounds, characterized in that biologically degradable polymers are mixed with active compounds, and optionally plasticizers and optionally customary additives and the mixture is processed in the customary manner.

4. A method of combating parasites on or around animals and plants by having the shaped articles according to claim 1 in the form of tapes, medallions or ear tags on or around the animals or their environment, followed by comminuting, granulating or grinding the shaped article and applying the same to the plants or their environment.

5. A method of combating parasites on or around animals and plants by having the shaped articles according to claim 2 in the form of tapes, medallions or ear tags on or around the animals or their environment, followed by comminuting, granulating or grinding the shaped article and applying the same to the plants or their environment.

6. The method of claim 4 characterized by employing the shaped articles, after comminuting, granulating or grinding, as soil granules for combating phytopathogenic insects in open air or indoor plants.

7. The method of claim 5 characterized by employing the shaped articles, after comminuting, granulating or grinding, as soil granules for combating pytopathogenic insects in open air or indoor plants.

* * * * *